United States Patent
Zapp et al.

(10) Patent No.: US 6,660,322 B2
(45) Date of Patent: Dec. 9, 2003

(54) METHOD FOR ENHANCING POST-PROCESSING CONTENT OF BENEFICIAL COMPOUNDS IN FOODSTUFFS MADE WITH COCOA BEANS

(76) Inventors: Loretta Zapp, c/o Oncology Sciences Corporation, 11120 Capitol of Texas Hwy S., Building Three, Suite 205, Austin, TX (US) 78746; Thomas J. Slaga, c/o AMC Cancer Research Center, 1600 Pierce St., Denver, CO (US) 80214; Jifu Zhao, c/o AMC Cancer Research Center, 1600 Pierce St., Denver, CO (US) 80214; Mark Lang, 4823 Mandarilla Way, Apex, NC (US) 27502

( * ) Notice: Subject to any disclaimer, the term of this patent is extended or adjusted under 35 U.S.C. 154(b) by 188 days.

(21) Appl. No.: 09/993,315

(22) Filed: Nov. 14, 2001

(65) Prior Publication Data

US 2002/0081363 A1 Jun. 27, 2002

(51) Int. Cl.$^7$ .............................. A23G 1/00; A23G 1/02
(52) U.S. Cl. ........................................ 426/631; 426/431
(58) Field of Search ................................. 426/631, 431, 426/466

(56) References Cited

U.S. PATENT DOCUMENTS

| | | |
|---|---|---|
| 3,114,641 A | 12/1963 | Sperti et al. |
| 3,657,424 A | 4/1972 | Aktins et al. |
| 3,799,049 A * | 3/1974 | Smith, Jr. |
| 4,053,652 A | 10/1977 | Mahlmann |
| 4,325,975 A | 4/1982 | Lindon et al. |
| 4,497,800 A | 2/1985 | Larson et al. |
| 4,722,847 A | 2/1988 | Heckert |
| 4,737,375 A | 4/1988 | Nakel et al. |
| 4,740,380 A | 4/1988 | Melachouris et al. |
| 4,851,221 A | 7/1989 | Pak et al. |
| 4,857,351 A | 8/1989 | Neilson et al. |
| 4,904,484 A | 2/1990 | Small et al. |
| 4,919,963 A | 4/1990 | Heckert |
| 4,985,271 A | 1/1991 | Neilson et al. |
| 5,232,709 A | 8/1993 | Saltman et al. |
| 5,716,649 A | 2/1998 | Nam |
| 6,045,843 A | 4/2000 | Gurol |
| 6,086,927 A | 7/2000 | Frielich et al. |
| 6,106,874 A | 8/2000 | Liebrecht et al. |
| 6,312,753 B1 | 11/2001 | Kealey et al. |

FOREIGN PATENT DOCUMENTS

| | | |
|---|---|---|
| EP | 0 075 114 B1 | 6/1985 |
| EP | 1370118 | 1/1986 |
| JP | 63-254950 | * 10/1988 |
| JP | 6-206785 | * 7/1994 |

OTHER PUBLICATIONS

Karim et al.; Effects of Cocoa Extracts on Endothelium—Dependent Relaxation; Journal of Nutrition (supplement to); 2000; 2105S–2108S; American Society for Nutritional Sciences.

Vinson et al.; Vitamins and Especially Flavonoids in Common Beverages Are Powerful in Vitro Antioxidants Which Enrich Lower Density Liproproteins and Increase Their Oxidative Resistance After ex Vivo Spiking in Human Plasma; J. Agric. Food Chem.; 1999; 2502–2504; v. 47; No. 7; American Chemical Society.

* cited by examiner

*Primary Examiner*—Anthony J. Weier
(74) *Attorney, Agent, or Firm*—David G. Henry

(57) ABSTRACT

A new cocoa bean processing technique which, in stark contrast to conventional cocoa processing methods, preserves the beneficial flavanoid compounds of cocoa beans in finished, cocoa bean-based foodstuffs. The present method produces roasted cocoa beans that can be ground and the liquor can be either cooled and allowed to solidify (unsweetened chocolate) or pressed and re-ground to form cocoa powder. The resulting cocoa powder can then be used in a traditional manner to make sweetened chocolate products such as candy and beverages for consumption by humans or animals. The resulting products will be a source of flavanoid compounds, which are known antioxidants.

8 Claims, No Drawings

US 6,660,322 B2

METHOD FOR ENHANCING POSTPROCESSING CONTENT OF BENEFICIAL COMPOUNDS IN FOODSTUFFS MADE WITH COCOA BEANS

CITATION TO PRIOR APPLICATION

This is a continuation-in-part with respect to U.S. application, Ser. No. 09/843,543 which was a continuation-in-part of U.S. application Ser. No. 09/481,279 which, in turn, was a continuation-in-part of U.S. application Ser. No. 09/468,560, from all of which priority is claimed under 35 U.S.C. §120.

BACKGROUND OF THE INVENTION

1. Field of the Invention

The present invention relates to food processing, and in particular to cocoa bean processing and its products.

2. Background Information

Test-tube studies by German scientists recently showed that the tetramers found in chocolate were highly beneficial in curbing the type of oxidation damage to blood vessel walls that arise from free-radicals in the blood stream. Chocolate's tetramers and larger procyanidins also help relax the inner surface of blood vessels, according to studies in isolated tissues headed by C. Tissa Kappagoda of the University of California, Davis School of Medicine.

Additionally, cocoa flavonoids have been found to be more powerful than vitamins, such as ascorbic acid, in limiting the oxidation of cholesterol circulating in low-density lipoproteins (LDLs) and very-low-density lipoproteins. December 1999 JOURNAL OF AGRICULTURAL AND FOOD CHEMISTRY Atherosclerosis studies have suggested that oxidation of these lipoproteins is an essential step in the creation of artery-clogging plaque.

The primary family of flavonoids contributing to the antioxidant activity of chocolates is the procyanidins. Their basic unit is a three-ring molecular structure. The mature cocoa bean contains pairs known as dimers, triads known as trimers, quartets known as tetramers, and larger ensembles of these units.

Cesar G. Fraga of the University of Buenos Aires hails the procyanidins' antioxidant activity. In work funded by Mars, he has demonstrated a rise of chocolate-derived procyanidins in the blood of men and women very shortly after eating semisweet-chocolate candies. Dr. Fraga's team found that blood sampled 2 hours after candy consumption protected its circulating lipids from oxidation. The more chocolate eaten, the better the protection, according to a fair reading of the study.

According to Dr. Fraga, earlier test-tube studies indicate that the procyanidins may function as a first line of defense against damaging oxidants—sparing vitamin C and other antioxidant vitamins that would otherwise be destroyed in the reactions. In these experiments, while all of the tested procyanidins appeared active, the pentamer offered the best protection.

As beneficial as the chocolate-derived compounds described above are, when conventionally processed, chocolate-based foodstuffs contain substantially lower levels of these compounds than do raw cocoa beans.

Fermentation and drying of cocoa beans bring about complex chemical changes, most notably, the formation of components required for the development of the characteristic flavor and color of cocoa. Fermentation, however, also significantly decreases the concentrations of polyphenolic compounds in the fermented cocoa beans, relative to the concentrations of polyphenolic compounds in unfermented or under-fermented beans.

Such traditional cocoa bean processing steps as roasting also reduces the cocoa polyphenol concentration in the cocoa powder or chocolate liquors produced thereby. The cocoa polyphenol concentration of chocolate also decreased during manufacture. The concentration of polyphenols in finished chocolates is approximately 20% to 60% lower than that calculated based on the polyphenol concentration of the cocoa powder or chocolate liquor used to prepare the chocolate.

In summary, conventional processing techniques do not provide food products, especially cocoa-containing confectioneries, that adequately retain the polyphenol concentrations of cocoa raw materials as would be necessary to benefit from the health benefits of such compounds.

In view of the foregoing, it would be of inestimable value to society to provide some method by which the concentrations of polyphenols, and in particular cocoa polyphenols, could somehow be conserved through the processing steps that lead to finished, cocoa-based foodstuffs.

Accordingly, it is an object of the present invention to provide a processing technique to prepare food products and confectioneries, particularly cocoa-containing confectioneries, that will conserve the cocoa polyphenol concentration of cocoa powders, chocolate liquors, or extracts thereof, in the finished, shelf-ready product It is another object of the present invention to provide a processing technique to prepare food products and confectioneries, particularly cocoa-containing confectioneries, containing polyphenolic acids and other beneficial compounds which are healthier than those existing cocoa containing confectioneries.

It is another object of the present invention to provide an improved cocoa containing confectionery which has more bioavailable polyphenol compounds than that of cocoa containing confectioneries which are processed by conventional methods.

It is another object of the present invention to provide improved cocoa containing confectioneries which have greater ability to quench oxidative stress and destroy free radicals than cocoa containing confectioneries which are processed by conventional methods.

It is another object of the present invention to provide an improved cocoa containing confectionery product which yields a more healthful end product than existing cocoa containing confectionery products.

In satisfaction of these and related objects, the method of the present invention avoids the significant and detrimental losses of polyphenols that occur during conventional cocoa processing by removing a significant amount of said polyphenols prior to fermentation and/or roasting and then adding a portion of these polyphenols back. The process of removing polyphenols before fermentation and/or roasting, and then adding them back after fermentation and/or roasting, yields products with significantly higher cocoa polyphenol concentrations than like products which are produced through conventional methods.

DETAILED DESCRIPTION OF THE PREFERRED EMBODIMENT

The process or method of the present invention is very simple, yet it is wholly unknown in the cocoa-related industries.

Raw cocoa beans are soaked in water prior to fermentation or roasting. At present, the process is believed to work equally well on cocoa beans as when used with coffee beans according to a like process of the same invention as the present one (subject of co-pending patent application(s)). Therefore, the following processes, although references are to coffee beans and beverages made from coffee beans, are illustrative of the processing of cocoa beans according to the present and herein claimed invention and of analogous, beneficial results which are to be experienced by practitioners of the present invention. Further research may reveal variations of the processes, with respect to coffee beans and/or cocoa beans, but such variations (time, heat, relative volumes, etc.) will amount to "fine tuning" and will certainly reside within the scope of the present invention as claimed.

EXAMPLE 1

Raw green coffee beans are pre-soaked in water for 3 hours at 75 deg C. 1000 grams of green beans soaked in 2000 mls of water. 1000 mls of pre-soak solution (water used for pre-soaking) was retained after beans are removed from water for roasting. Pre-soaked green beans are roasted in a traditional coffee roaster with temperature starting at 350 deg F. and increasing to 430 deg F. over a period of approximately 15–18 minutes.

At the conclusion of the roast, the beans are dropped into a container and immediately quenched with 150 mls of the pre-soak solution. The roasted beans are then ground to a powder and brewed with hot water to produce a coffee beverage.

Chemical analysis showed that the new beverage contains over 20%–65% of the pre-roasted phenolic acid content, specifically representing chlorogenic acid content at 40%–150% (depending on degree of roast—bigger increase with darker roast) over that in traditional roasted coffee of a similar roast color;

EXAMPLE 2

Raw green coffee beans are pre-soaked in water for 3 hours at 80 deg C. 1000 grams of green beans soaked in 2000 mls of water. 1000 mls of pre-soak solution was obtained Pre-soak water is collected for later quenching step. 1400 grams of regular green beans are roasted in a traditional manner. Upon completion of the roast the beans are split into a control and an experimental group and subsequently quenched with either 150 mls of water (control) or 150 mls of the pre-soak solution that has been previously collected from green beans. (experimental). The green beans used to create the pre-soak quenching solution are not the beans that are use in the roasting. The roasted beans are then ground to a powder and brewed with hot water to produce a coffee beverage.

Chemical analysis showed that the new beverage contains over 20%–70% of phenolic acid content, representing a 40%–200% chlorogenic acid content over that of the control of the same roast.

EXAMPLE 3

Raw green coffee beans are pre-soaked in water for 3 hours at 80 deg C. 1000 grams of green beans soaked in 2000 mls of water. 1000 mls of pre-soak solution was obtained. Pre-soak water is collected for later quenching step. A portion of the pre-soak water is collected and freeze dried to be used as a fortifying ingredient in the pre-soak quench. 1400 grams of regular green beans are roasted in a traditional manner. Upon completion of the roast the beans are split into a control and an experimental group and subsequently quenched with either 150 mls of water (control) or 150 mls of the pre-soak which has been fortified with 10 grams of freeze dried pre-soak. All pre-soak solution has been previously collected and/or collected and freeze dried from green beans. (experimental). The green beans used to create the pre-soak quenching solution are not the beans that are use in the roasting. The roasted beans are then ground to a powder and brewed with hot water to produce a coffee beverage.

Chemical analysis showed that the new beverage contains over 120% of phenolic acids, representing approx 250% of chlorogenic acid content of conventionally processed coffee;

The powder from the preceding examples can be sold as coffee powder for brewing or can be brewed and sold as a ready-to-drink coffee beverage. The resulting product can be taken as a food or functional food by a human or other mammal, orally.

The processes of the present invention when applied to cocoa beans represent significant departures from conventional production of cocoa, where green beans are simply roasted and/or fermented, and may or may not be quenched with water, whereas the end product of the present invention achieves a chemical profile of increased amounts of phenolic acids and other beneficial compounds which is different from existing cocoa-based foodstuffs. This new process yields, in cocoa-based products, more active, more bioavailable, and larger quantities of phenolic compounds than found in identical products which are produced through conventional processes.

Although the invention has been described with reference to specific embodiments, this description is not meant to be construed in a limited sense. Various modifications of the disclosed embodiments, as well as alternative embodiments of the inventions will become apparent to persons skilled in the art upon the reference to the description of the invention. It is, therefore, contemplated that the appended claims will cover such modifications that fall within the scope of the invention.

I claim:

1. A method for enhancing polyphenolic acid content in post-processing cocoa-based foodstuffs comprising the steps of:

selecting a measure of substantially raw cocoa beans;

immersing said cocoa beans in a pre-soak liquid containing water;

removing said cocoa beans from said pre-soak liquid;

processing said cocoa beans;; and quenching said cocoa beans substantially immediately after said processing with a portion of said pre-soak liquid.

2. The method of claim 1 wherein said processing is by roasting.

3. The method of claim 1 wherein said processing is by fermenting.

4. The method of claim 1 wherein said processing is by a combination of roasting and fermenting.

5. A method for enhancing polyphenolic acid content in post-processing cocoa beans comprising the steps of:

selecting a first measure of polyphenolic containing substrate;

immersing said first measure of polyphenolic containing substrate in a pre-soak liquid containing water;

collecting said pre-soak liquid after said immersing;

processing a second measure of cocoa beans; and quenching said second measure of cocoa beans after said processing with a portion of said pre-soak liquid.

6. The method of claim 5 wherein said processing is by roasting.

7. The method of claim 5 wherein said processing is by fermenting.

8. The method of claim 5 wherein said processing is by a combination of roasting and fermenting.

\* \* \* \* \*